(12) United States Patent
Akagi

(10) Patent No.: US 7,162,068 B2
(45) Date of Patent: Jan. 9, 2007

(54) MEDICAL IMAGE DISPLAYING DEVICE, IMAGE OBTAINING AND DISPLAYING DEVICE, METHOD FOR DISPLAYING IMAGE IN DISPLAYING DEVICE, AND PROGRAM FOR SELECTING DISPLAY FORMAT

(75) Inventor: Eiichi Akagi, Hino (JP)

(73) Assignee: Konica Corporation, Tokyo (JP)

(*) Notice: Subject to any disclaimer, the term of this patent is extended or adjusted under 35 U.S.C. 154(b) by 256 days.

(21) Appl. No.: 10/341,203

(22) Filed: Jan. 13, 2003

(65) Prior Publication Data

US 2003/0142119 A1 Jul. 31, 2003

(30) Foreign Application Priority Data

Jan. 29, 2002 (JP) ............................. 2002-019406

(51) Int. Cl.
*G06K 9/00* (2006.01)
*G06F 15/00* (2006.01)

(52) U.S. Cl. ....................... 382/132; 382/131; 715/517

(58) Field of Classification Search ................ 345/788, 345/765, 619; 382/131, 132; 715/517
See application file for complete search history.

(56) References Cited

U.S. PATENT DOCUMENTS

| | | | | |
|---|---|---|---|---|
| 3,859,527 A | | 1/1975 | Luckey | |
| 5,060,170 A | * | 10/1991 | Bourgeois et al. | 345/788 |
| 5,644,611 A | * | 7/1997 | McShane et al. | 378/98 |
| 5,779,634 A | * | 7/1998 | Ema et al. | 600/407 |
| 5,856,821 A | * | 1/1999 | Funahashi | 345/667 |
| 5,954,650 A | * | 9/1999 | Saito et al. | 600/425 |
| 5,986,662 A | * | 11/1999 | Argiro et al. | 345/424 |
| 5,987,345 A | * | 11/1999 | Engelmann et al. | 600/407 |
| 6,069,653 A | * | 5/2000 | Hudson | 348/143 |
| 6,081,267 A | * | 6/2000 | Stockham et al. | 715/788 |
| 6,188,407 B1 | * | 2/2001 | Smith et al. | 715/841 |
| 6,462,776 B1 | * | 10/2002 | Hudson | 348/159 |
| 6,469,717 B1 | * | 10/2002 | Wineke et al. | 345/788 |
| 6,734,880 B1 | * | 5/2004 | Chang et al. | 715/738 |
| 6,823,203 B1 | * | 11/2004 | Jordan | 600/407 |

FOREIGN PATENT DOCUMENTS

JP 55-12144 A 1/1980

* cited by examiner

*Primary Examiner*—Kee M. Tung
*Assistant Examiner*—Michelle K. Lay
(74) *Attorney, Agent, or Firm*—Frishauf, Holtz, Goodman & Chick, P.C.

(57) ABSTRACT

A medical image displaying device for displaying a plurality of image data obtained by photographing a patient, includes: a plurality of display formats for designating at least one selected between each display size of the plurality of image data and each display position of the plurality of image data.

34 Claims, 14 Drawing Sheets

FIG.8

MEDICAL IMAGE DISPLAYING DEVICE, IMAGE OBTAINING AND DISPLAYING DEVICE, METHOD FOR DISPLAYING IMAGE IN DISPLAYING DEVICE, AND PROGRAM FOR SELECTING DISPLAY FORMAT

BACKGROUND OF THE INVENTION

1. Field of the Invention

The present invention relates to a medical image displaying device and a method for displaying image data. In particular, the present invention relates to an image obtaining and displaying device for reading and displaying a diagnostic image data, such as a radiographic image, stored in a diagnostic image conversion medium, a method for displaying the images in the above device, and a program for selecting a display format.

2. Description of Related Art

A radiographic image obtained by using radiation, such as X-ray or the like, has been used widely as a medical image for diagnosing diseases. For example, so-called X-ray photograph by which development is performed by irradiating the X-ray transmitted through a subject to a phosphor layer (phosphor screen) and irradiating the visible light generated in the phosphor layer to a film, in which silver salts are used like usual photograph, has been used in earlier technology.

However, recently, a radiographic image generating method for taking out a radiographic image as a digital signal directly from a radiation detector, such as a stimulating phosphor, an FPD (Flat Panel Detector) or the like, has been used instead of a film coated with silver salts. The radiographic image obtained by the radiographic image generating method is processed variously so as to be more suitable for the diagnosis.

Concretely, for example, a radiographic image converting method in which a stimulating phosphor is used and visible rays or infrared rays are used as stimulating excitation lights, is disclosed in the U.S. Pat. No. 3,859,527 and the Japanese Patent Laid-Open Publication No. 55-12144. In this method, a radiographic image conversion plate in which a stimulating phosphor layer is formed on a supporting member is used. The radiation transmitted through a subject is irradiated to this stimulating phosphor layer, and a latent image is formed by accumulating the radiation energy corresponding to the quantity of radiation transmitted through each body part of the subject. Thereafter, the stimulating phosphor layer is scanned by a stimulating excitation light, such as laser beam having a predetermined wavelength or the like, and the accumulated radiation energy is emitted as a stimulating light. Then, the stimulating light is converted photoelectrically into electric signals by using a photoelectric transducer, such as photomultiplier or the like, and the electric signals are taken out.

The radiographic image diagnostic system utilizing the stimulating phosphor is commonly referred to as "Computed radiography (CR)" can be roughly classified into two types. One is an erect/supine exclusive use type of system that a radiographic image converting plate is incorporated into a reading device. The other is a cassette type of system comprising a portable cassette containing the stimulating phosphor therein and a reading device for reading an image by pulling out the stimulating phosphor from the cassette. The above-described cassette type of radiographic image diagnostic system will be explained with reference to FIG. 15.

As shown in FIG. 15, the cassette type of radiographic image diagnostic system 201 comprises an X-ray photographic room 204 for photographing a subject M, a portable cassette 217 into which a radiographic image conversion plate having a stimulating phosphor sheet 24 is incorporated, a reader 202 for reading a radiographic image from the cassette 217 and a console 203 for controlling the reader 202, displaying an image data and inputting a photographing condition, a reading condition and the like.

In the X-ray photographic room 204, the subject M is positioned between a radiation source 204a and the cassette 217. When the radiation is irradiated from the radiation source 204a, the stimulating phosphor sheet 24 contained in the cassette 217 accumulates a part of irradiated radiation energy. After the photographing, when the cassette 217 is set to the reader 202, the reader 202 irradiates an excitation light to the stimulating phosphor sheet 24 contained in the cassette 217. By the irradiated excitation light, a stimulating light emitted in accordance with the accumulated radiographic image information is photoelectrically converted. After the A/D conversion, a signal is outputted as a digital image data.

The console 203 controls the reading operation of the reader 202 and comprises a monitor for inputting information, such as patient information, a region to be photographed and the like and for confirming the read image. In the monitor, for example, a reception list screen for displaying information list relating to a registered patient, a register/search screen for registering a new patient and for inputting a predetermined search condition to search the patient information, a region-to-be-photographed selecting screen for setting region-to-be-photographed information for the selected patient, an image data displaying screen for displaying the obtained image and the like are displayed in order. By using the image data displaying screen, the patient is diagnosed. In general, in the image data displaying screen, a display format in which one main image data is largely displayed and the other related obtained image data are displayed smaller in a thumbnail style is adopted.

The regions of body, which are photographed by such a radiographic image diagnostic system 201, are various ones, such as the chest, abdomen, lumbar spine, head and the like. Further, when the chest is exemplified, the chest has a plurality of areas, such as ribs, lateral surface of sternum, oblique position of sternum, clavicle, sternoclavicular joint and the like. The suitable display format for the diagnosis differs according to the region or the area. Even though the same region or area is photographed, the most suitable display format differs because the number of photograph sheets and the object of the photographing differ according to the condition of the patient.

Concretely, for example, when the anteroposterior surface of an abdomen is photographed, in order to confirm whether the image is obtained in a correct position and in a suitable contrast, one image is largely displayed immediately after the one image is obtained. When a plurality of images are obtained, the other images except the one large image are displayed so as to arrange them in a small size. However, when a lumbar spine is photographed in four directions (anteroposterior surface, lateral surface, right oblique position and left oblique position), the diagnosis is easily performed not by using the images separately but by comparing a plurality of images with each other in order to generally judge whether the images are obtained in a correct position and in a suitable contrast.

In such a case, because the format that one main image data was largely displayed, was generally used in a conventional device, the obtained image data was displayed in the same display format regardless of a region to be photographed. As a result, there was a problem that a suitable diagnosis was not easily performed. The various display formats of the image data are an important technology, in particular, in a medical field in which a radiographic image is used. The display formats are indispensable for improving the convenience of the diagnosis and for enabling a suitable diagnosis.

SUMMARY OF THE INVENTION

In order to solve the above-described problems, an object of the present invention is to provide a medical image displaying device and an image obtaining and displaying device for suitably selecting a display format of an image data in accordance with a region to be photographed, a condition of a patient, the number of photograph sheets and the like, and to provide a method for displaying image in the displaying device and a program for selecting the display format.

That is, in accordance with the first aspect of the present invention, a medical image displaying device for displaying a plurality of image data obtained by photographing a patient, comprises:

a plurality of display formats for designating at least one selected between each display size of the plurality of image data and each display position of the plurality of image data.

In accordance with the second aspect of the present invention, an image obtaining and displaying device comprises:

a reading unit for reading a plurality of image data obtained by photographing a patient, from a diagnostic image conversion medium for storing diagnostic image, and a display unit for displaying the image data;

wherein the display unit comprises: a storing section for storing a plurality of display formats for designating at least one selected between each display size of the plurality of image data and each display position of the plurality of image data; a selecting section for selecting a specified display format from the plurality of image data; and a display and preparing section for displaying the image data and preparing a display screen in accordance with the specified display format selected by the selecting section.

The "diagnostic image" is not limited to a radiographic image obtained by using a radiation, such as X-ray, and includes images obtained by an optional photographic device used in a medical field, such as images obtained by photographing a patient with magnetism, supersonic waves, or the like.

In the present invention, it is preferable that each of the plurality of display formats comprises a screen changing section for commanding the device to change one display format to another display format so as to change one display format to another display format on the screen.

In the present invention, it is preferable that history information is stored in the storing section; the history information correlating the specified display format with at least one specified information selected from the group consisting of the reading unit, the display unit, a type of the diagnostic image conversion medium, a type of a cassette, date and time of a photographing, an operator, and supplementary information of a schedule for the photographing; and the selecting section comprises a corresponding display format selecting section for selecting a corresponding display format corresponding to the history information. Further, it is preferable that setting information is previously registered in the storing section; the setting information correlating the specified display format with at least one specified information selected from the group consisting of the reading unit, the display unit, a type of the diagnostic image conversion medium, a type of a cassette, date and time of a photographing, an operator, and supplementary information of a schedule for the photographing; and the selecting section comprises a corresponding display format selecting section for selecting a corresponding display format corresponding to the setting information. It is preferable that the supplementary information of the schedule for the photographing comprises at least one selected from the group consisting of number of image data to be obtained, a region to be photographed, a name of a doctor, and a department.

In the present invention, the plurality of display formats may comprise at least a first display format in which one image data is displayed in a first size and the other image data are displayed in a second size which is smaller than the first size; and a second display format in which the plurality of image data are displayed so as to be arranged in a same size. The plurality of display formats may comprise at least a second display format in which the plurality of image data are displayed so as to be arranged in a same size.

In the present invention, the first display format may comprise at least one function selected between (a) a first function in which when a first image data is obtained, the obtained first image data is displayed in the first size and when a second image data displayed in the second size is selected, the selected second image data is displayed in the first size; and (b) a second function in which when the first image data is obtained, the obtained first image data is displayed in the second size and when the second image data displayed in the second size is selected, the selected image data is displayed in the first size.

In the present invention, the second display format may comprise at least a parallel display format for displaying even number of image data selected from the plurality of image data so as to be arranged in parallel. The second display format may comprise at least one parallel display format selected from the consisting of a first parallel display format for displaying two image data selected from the plurality of image data so as to be arranged in parallel; a second parallel display format for displaying four image data selected from the plurality of image data so as to be arranged in parallel; and a third parallel display format for displaying eight image data selected from the plurality of image data so as to be arranged in parallel. In the parallel display format, it is preferable that the image data selected from the plurality of image data are displayed and the image data except the selected image data are displayed by changing the position and/or the size on the screen.

In accordance with the third aspect of the present invention, a method for displaying a plurality of image data in a medical image device having a function of displaying the plurality of image data obtained by photographing a patient, comprises: providing a plurality of display formats for designating at least one selected between each display size of the plurality of image data and each display position of the plurality of image data so as to select a display screen.

In accordance with the fourth aspect of the present invention, a method for displaying a plurality of image data in an image reading device for reading the plurality of image data obtained by photographing a patient, from a diagnostic image conversion medium for storing diagnostic image, and for displaying the read image data; comprises: storing a plurality of display formats for designating at least one selected between each display size of the plurality of image data and each display position of the plurality of image data; selecting a specified display format from the plurality of image data; and displaying the image data and preparing a display screen in accordance with the specified display format.

In accordance with the fifth aspect of the present invention, a computer-executable program for executing any one of the above-described methods for displaying the plurality of image data.

According to the present invention, a plurality of display formats, such as a format in which one image data is displayed in a large size and the other image data are displayed in a small size in a thumbnail style, are stored. The image data are displayed in the display format selected by an operator in accordance with the condition of the patient or the region to be photographed or in the display format which is automatically selected by the program in accordance with the history information. One display format can be changed to another display format. Therefore, it is possible to carry out a more precise diagnosis.

BRIEF DESCRIPTION OF THE DRAWINGS

The present invention will become more fully understood from the detailed description given hereinbelow and the accompanying drawings which are given by way of illustration only, and thus are not intended as a definition of the limits of the present invention, and wherein;

FIG. 8 is a view showing an example of a photographing condition selecting screen displayed on the console according to the first embodiment of the present invention;

PREFERRED EMBODIMENT OF THE INVENTION

As a preferred embodiment, the image obtaining and displaying device according to the present invention, comprises at least a reading unit for reading a plurality of image data obtained by photographing a patient, from a radiographic image conversion medium, such as a cassette containing a radiographic image conversion plate, for storing radiographic image, and a display unit for displaying the image data; wherein the display unit comprises: a storing section for storing a plurality of display formats for designating at least one selected between each display size of the plurality of image data and each display position of the plurality of image data; a selecting section for selecting a specified display format from the plurality of image data; and a display and preparing section for preparing a display screen by fitting the plurality of image data into the selected display format so as to display the image data in the suitable display format in accordance with the condition of the patient or the region to be photographed. Further, the accuracy of the diagnosis can be improved by changing one display format to another freely. By executing a display format selecting program, a display format adopted in a previous diagnosis is extracted in accordance with history information. Therefore, the image data can be always displayed in a suitable display format.

In order to explain the above-described embodiment of the present invention in detail, the embodiments of the present invention will be explained with reference to the attached drawings.

Figure 1:
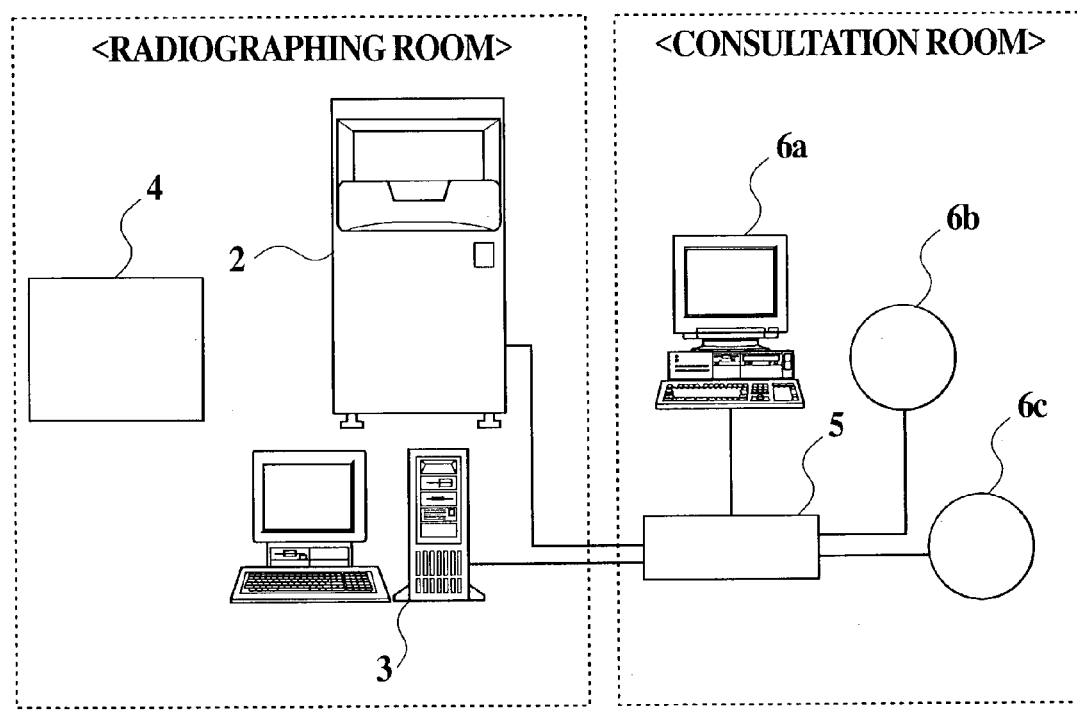
FIG. 1 is a view showing an arrangement of the radiographic image diagnostic system.
Figure 2:
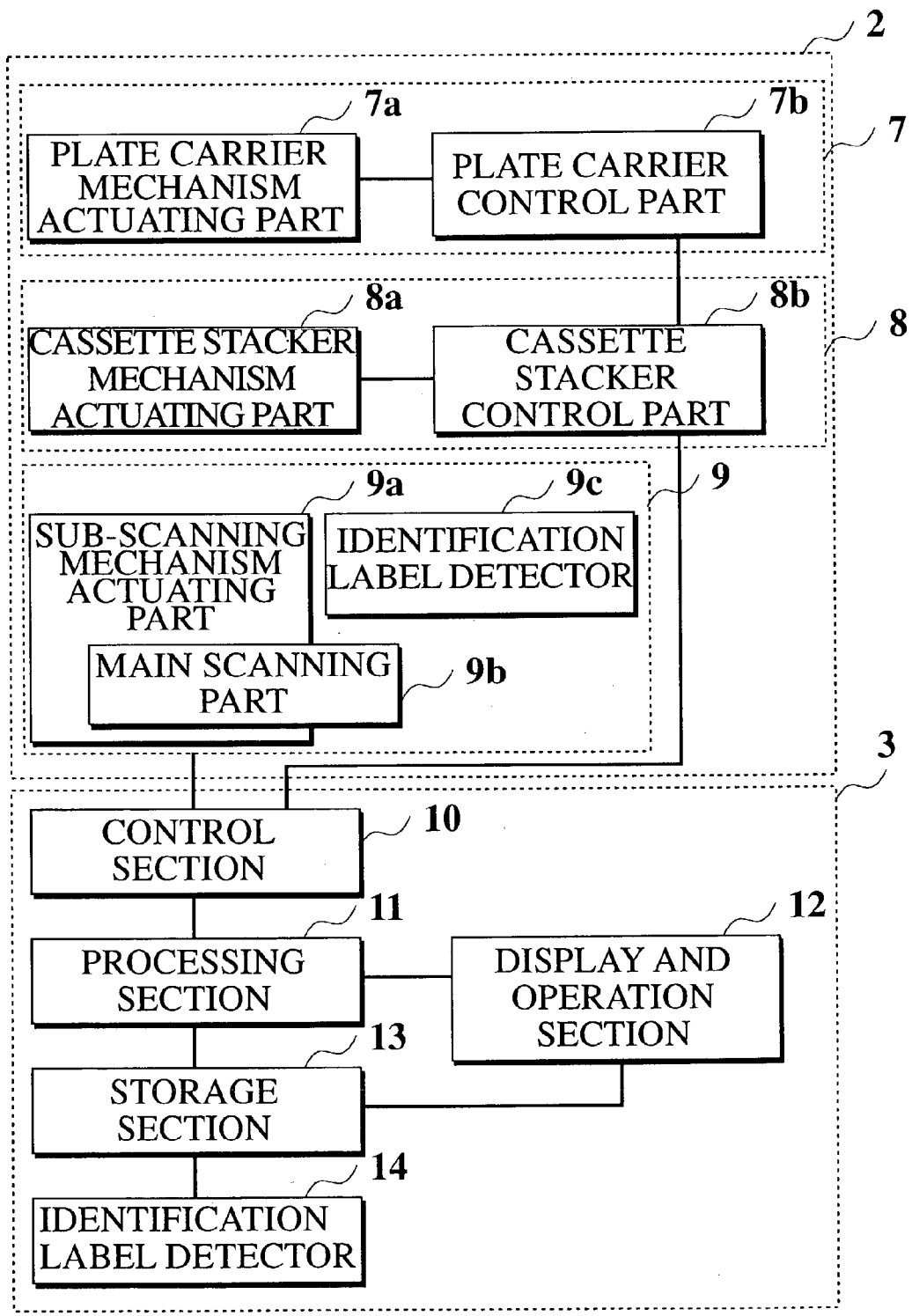
FIG. 2 is a block diagram showing an arrangement of the reader and that of the console according to the first embodiment of the present invention.
Figure 3A:
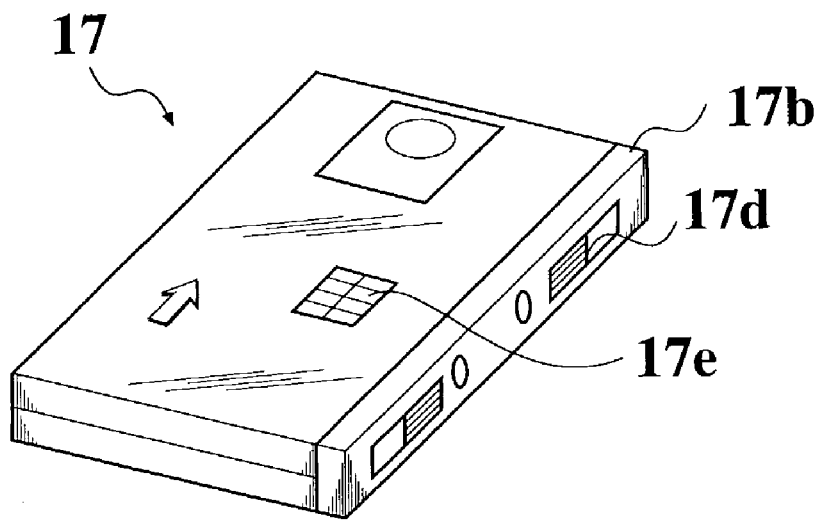
FIGS. 3A and 3B are perspective views showing a structure of the cassette.
Figure 3B:
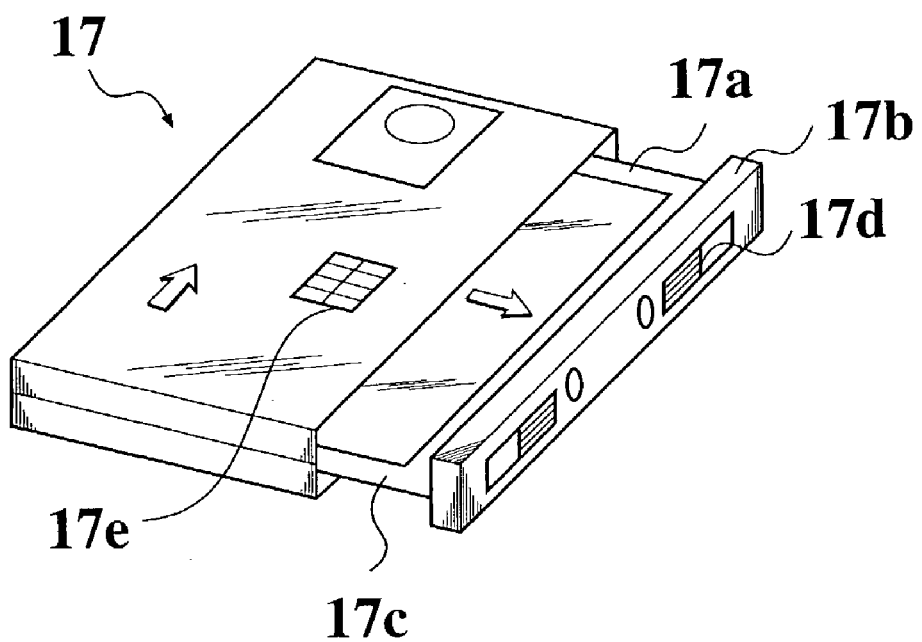
Figure 4:
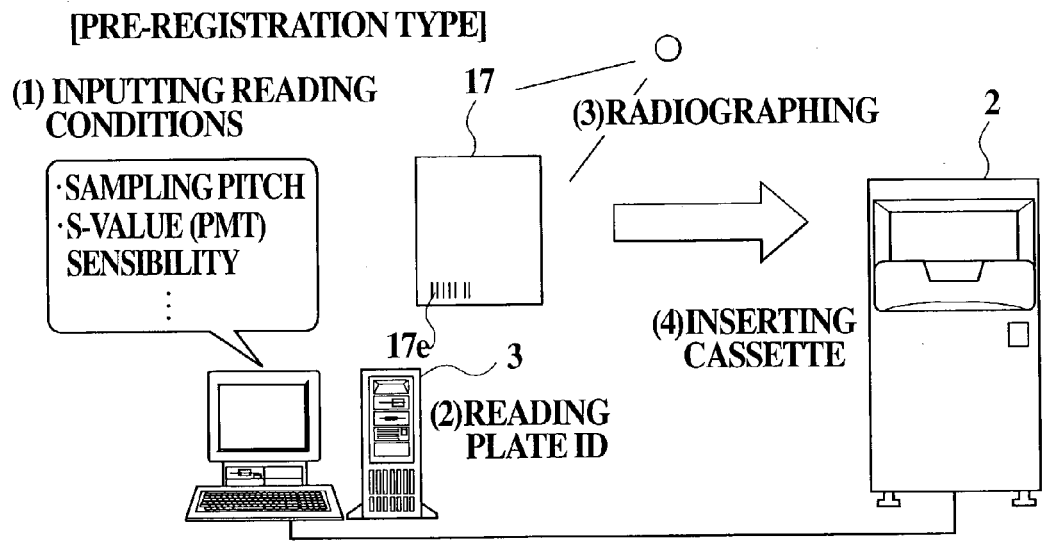
FIG. 4 is a view showing a pre-registration type of image reading process.
Figure 5:
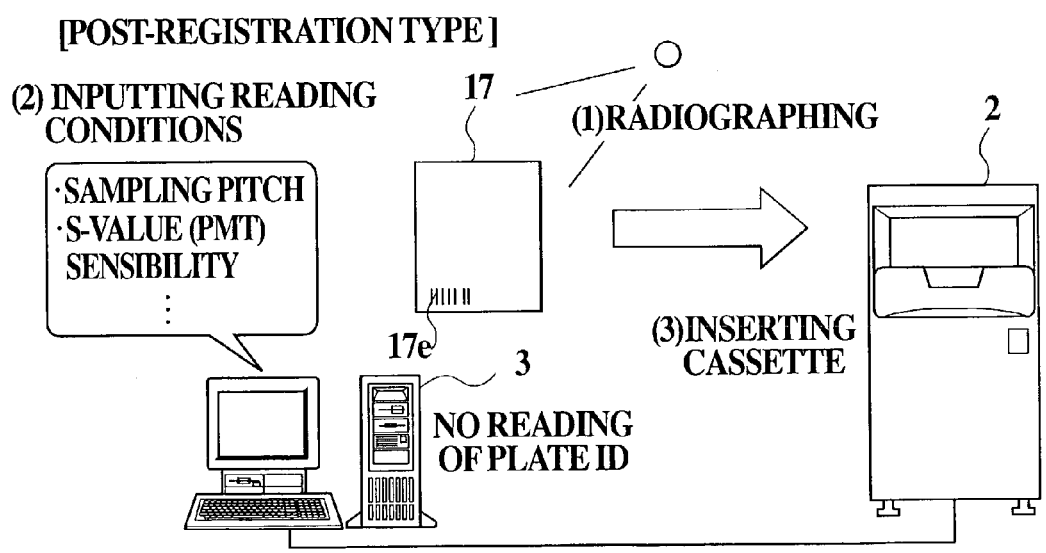
FIG. 5 is a view showing a post-registration type of image reading process.
Figure 10:
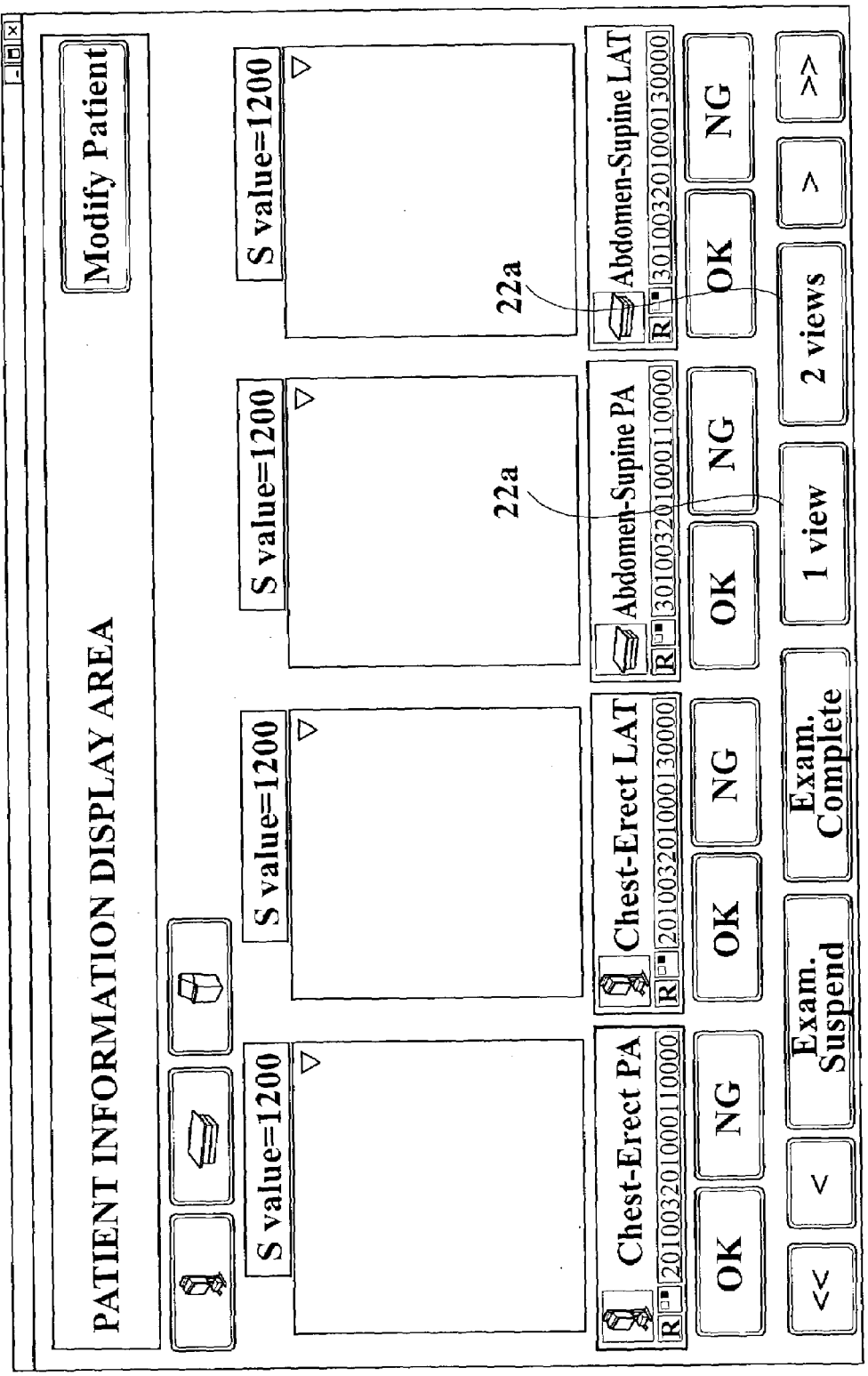
FIG. 10 is a view showing an example of an image data display screen (4 views display format) displayed on the console according to the first embodiment of the present invention.
Figure 11:
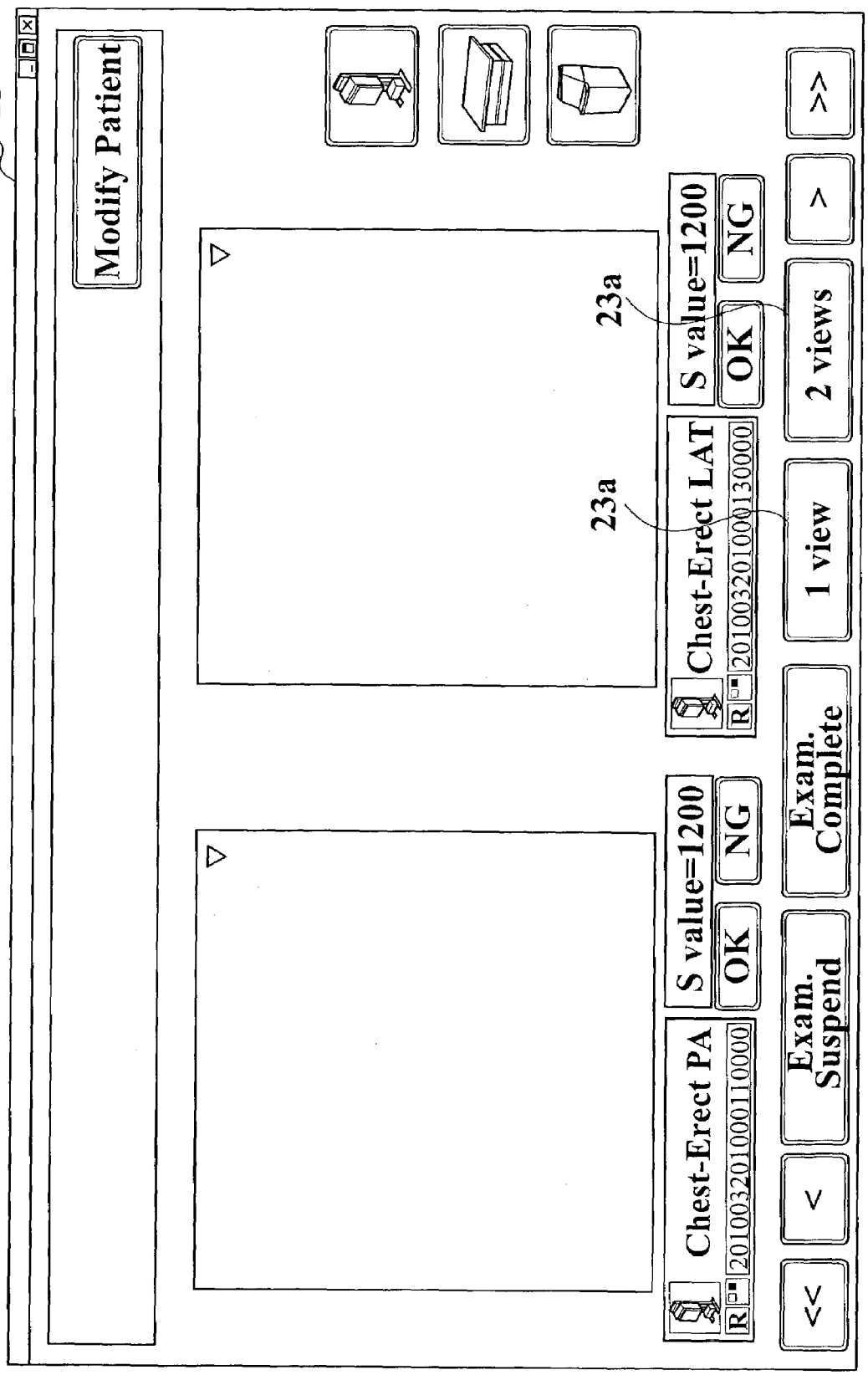
FIG. 11 is a view showing an example of an image data display screen (2 views display format) displayed on the console according to the first embodiment of the present invention.
Figure 12:
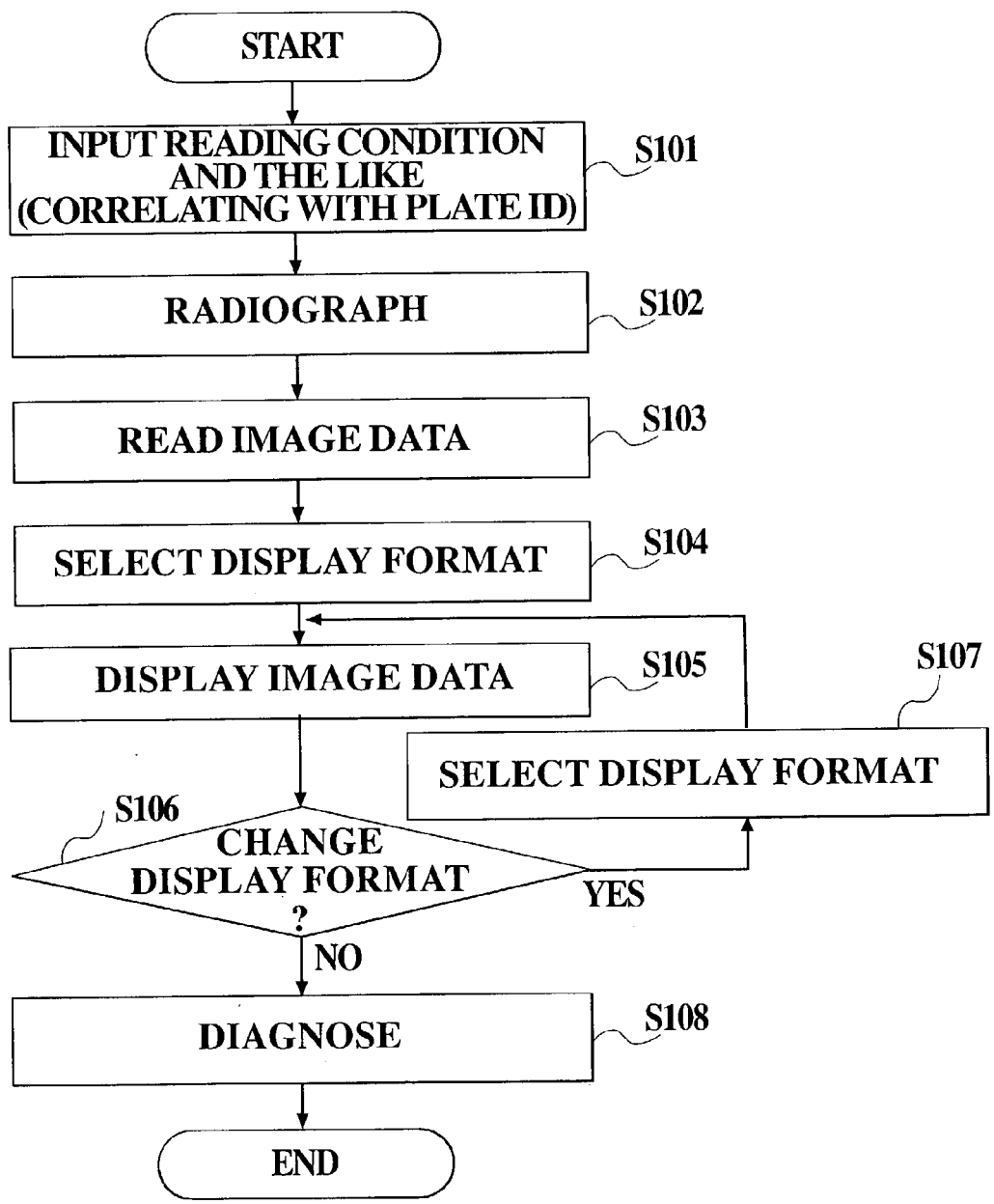
FIG. 12 is a flowchart showing a process for the image displaying method according to the first embodiment.

First Embodiment:

An image obtaining and displaying device (image reading device) according to the first embodiment of the present invention, a method for displaying a plurality of image data in the device and a display format selecting program will be explained with reference to FIGS. 1 to 12. FIG. 1 is a view showing an arrangement of the radiographic image diagnostic system for realizing the image display according to the present invention. FIG. 2 is a block diagram showing an arrangement of the image reading device (the reader and the console). FIGS. 3A and 3B are perspective views showing a structure of the cassette. FIGS. 4 and 5 are views for explaining two registration types of the reading condition in the image reading process. FIGS. 6 to 11 are views showing each example of screens displayed on the console constituting the image reading device according to the first embodiment. FIG. 12 is a flowchart showing a process for the image displaying method according to the first embodiment.

In the following explanation, an example in which the image display method according to the present invention is adapted for a cassette type of image reading device, is described. However, the present invention is not limited to the following example. The present invention can be adapted to an optional device for displaying a medical image, such as a system using other radiographic image conversion media, an erect/supine exclusive use type of system in which a radiographic image conversion medium is not used, a system for directly fetching the radiographic image as a digital signal by using a radiation detector, such as an FPD.

In order to easily understand the method for displaying image data, which is the feature of the present embodiment, firstly, each arrangement of the radiographic image diagnostic system and the image reading device and each function thereof will be explained.

As shown in FIG. 1, in the radiographic image diagnostic system 1 of the present embodiment, a reader 2 for reading a radiographic image from a cassette in which a latent image is formed by a device disposed in an X-ray photographic room 4, a console 3 for controlling the reading operation of the reader 2, for displaying the read image and for inputting patient information, region-to-be-photographed information, the reading condition and the like, are connected through a switching HUB 5 by LAN. In case of necessity, a printer 6c, a viewer 6b, a patient reception terminal 6a and the like are disposed. These devices are connected with other medical apparatus which is not shown, by a network, such as a DICOM or the like.

In the drawing, the reader 2 is separated from the console 3. However, the reader 2 and the console 3 may be incorporated so as to constitute the image reading device. Further, the reader 2 and the console 3 may be disposed in each photographing room. In another case, only the console 3 is disposed in the photographing room and the reader 2 is centralized in another place. The disposing position, the arrangement of the connections between the above-described devices, and the like, can be optionally set.

As shown in FIG. 2, the reader 2 for reading the image data obtained by the radiographic image photographing device comprises a cassette stacker section 8 for controlling the insertion of a cassette 17, a plate control section 7 for controlling the carrier of the radiographic image conversion plate, and an image reading section 9 for reading a latent image by scanning the radiographic image conversion plate.

The cassette stacker section 8 comprises a cassette stacker mechanism actuating part 8a and a cassette stacker control part 8b, can set a plurality of types of cassettes 17. In the plate control section 7, a plate carrier mechanism actuating part 7a and a plate carrier control part 7b are provided. The plate carrier control part 7b is controlled in accordance with a command from the cassette stacker control part 8b. The plate carrier mechanism actuating part 7a withdraws the radiographic image conversion plate from the cassette 17 to carry it toward the image reading section 9. In the image reading section 9, a sub-scanning mechanism actuating part 9a and a main scanning part 9b and an identification label detector 9c are provided. By the sub-scanning mechanism actuating part 9a, the main scanning part 9b is carried in a sub-scanning direction. By the laser scan of the main scanning part 9b, the image is read. Further, by the identification label detector 9c, information (plate ID) of the identification label attached to the cassette 17 is read.

The console 3 for controlling the reading operation of the reader 2, for inputting patient information, region-to-be-photographed information, the reading condition and the like, and for displaying the read image, comprises a control section 10 for controlling the reader 2 in accordance with the set reading condition; a processing section 11 for carrying out various image processing (correction processing, contrast transformation processing, trimming, reverse/rotation, changing of each parameter, masking or the like) for the image read by the reader 2; a display and operation section 12 for displaying a reception list, image data and the like, for setting patient information, region-to-be-photographed information, a reading condition or the like and for selecting a display format for the image data; a storage section 13 for storing a plurality of formats which are the base of the display format, and the like; and an identification label detector 14 for reading a plate ID of the cassette 17.

As described below, the display formats which are stored in the storage section 13 is a format for setting each arrangement of a plurality of image data and each display size thereof. A display screen is prepared by fitting the image data in the format selected by an operator with the display and operation section 12.

In the above-described cassette type of radiographic image diagnostic system 1, in order to specify the correlation between the cassette 17 and the patient information (schedule information), either a process (pre-registration) for carrying out the photographing after the correlation between the cassette 17 and the patient information is registered, or a process (post-registration) for correlating the inserting order of the cassette with the inputting order of the patient information without registering the cassette 17 before the radiographing, is adopted. Then, the image data is read.

In case of the pre-registration type, as shown in FIG. 4, firstly, an operator, such as a radiation engineer or the like, inputs the reading condition (sampling pitch, reading sensibility or the like) for reading the image with the reader 2, by using the display and operation section 12 of the console 3 (as shown in (1) of FIG. 4). Then, the information (hereinafter, referred to as "plate ID") of the identification label 17e (see FIGS. 3A and 3B) attached to the cassette 17 is read by the identification label detector 14 of the console 3 (as shown in (2) of FIG. 4). The inputted reading condition is correlated with the plate ID. The reading condition and the plate ID are stored. Thereafter, the radiographing is carried out by using the registered cassette 17 (as shown in (3) of FIG. 4). The cassette 17 in which a latent image is formed is inserted into the reader 2 (as shown in (4) of FIG. 4). In the reader 2, the plate ID of the cassette 17 is read by the incorporated identification label detector 9c. The reading condition correlating with the plate ID is searched and obtained. The image is read in the above reading condition.

In case of the post-registration type, as shown in FIG. 5, firstly, an operator, such as a radiation engineer or the like, carries out the X-ray photographing (as shown in (1) of FIG. 5). Thereafter, the operator inputs the reading condition for reading the image with the reader 2, by using the display and operation section 12 of the console 3 (as shown in (2) of FIG. 5). In case of the post-registration type, because the plate ID is not correlated with the reading condition, it is not necessary to read the plate ID. Then, the cassette 17 in which a latent image is formed is inserted into the reader 2 (as shown in (3) of FIG. 5). In the console 3, the inputting order of the reading condition is assigned to the inserting order of the cassette in sequence. The reading condition correlating to the inserted cassette 17 is determined. The image is read in the determined reading condition.

The pre-registration and the post-registration have each feature. For example, in a hospital or the like, in which many readers 2 and consoles 3 are provided in each place and many radiation engineers carry out the photographing, it is possible to suitably carry out the radiographic image diagnosis for many patients by the pre-registration. On the other hand, in case that a medical practitioner or the like has a small number of the readers 2 and a small number of the consoles 3 and a small number of the radiation engineers carry out the radiographic image diagnosis, it is possible to carry out the X-ray photographing rapidly and effectively by the post-registration. The image display method which is the feature of the present invention, can be adapted to the both registration types.

The process from the X-ray photographing for a patient to the displaying of the X-ray image, which is carried by using the above system, will be explained with reference to each example of the screens shown in FIGS. 6 to 11 and the flowchart shown in FIG. 12. The following explanation is described about the process in which the image data is read by the pre-registration. However, even in the post-registration, the operation after the reading of the image data is the same as the operation carried out in the pre-registration.

Figure 6:
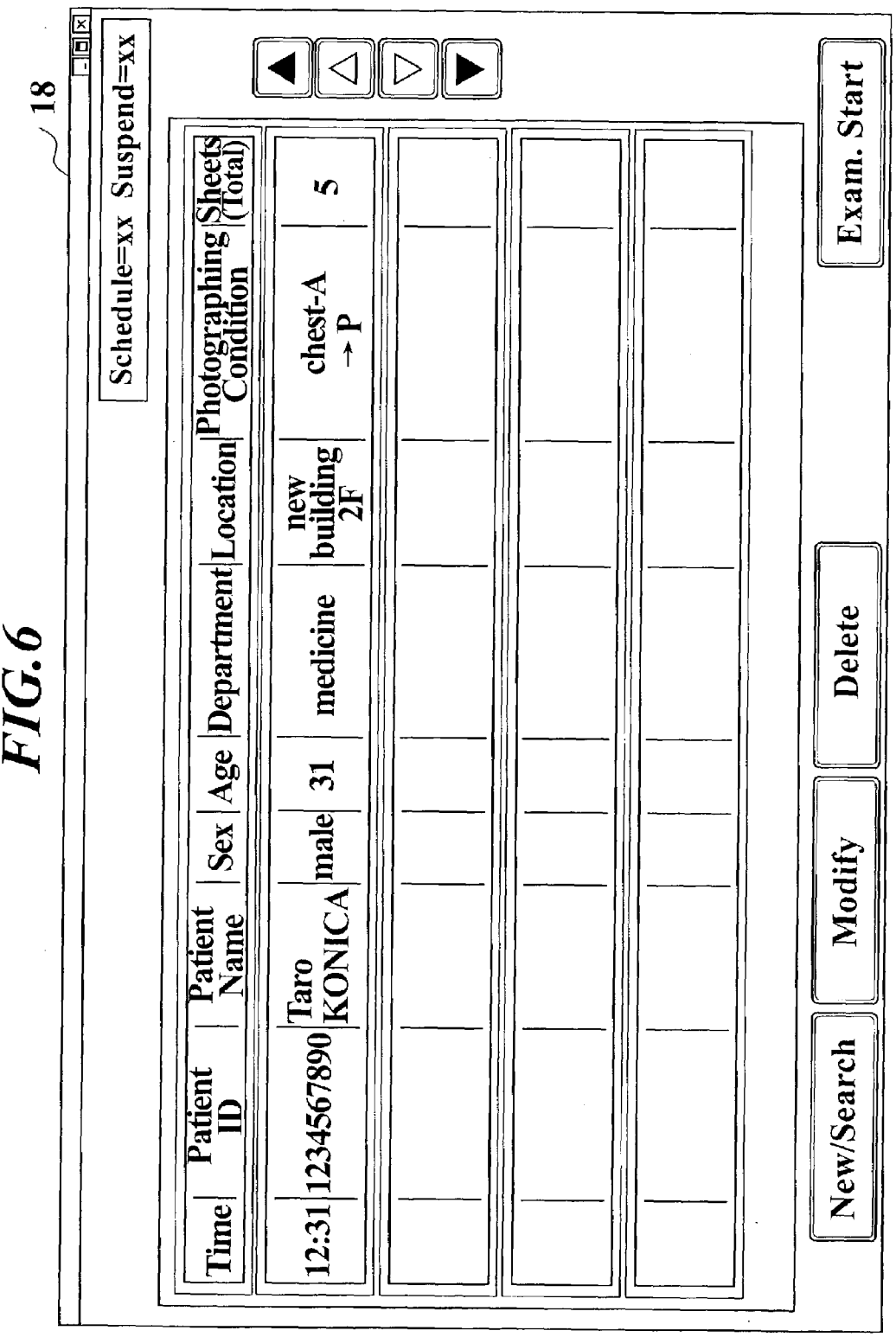
FIG. 6 is a view showing an example of a reception list screen displayed on the console according to the first embodiment of the present invention.
Figure 7:
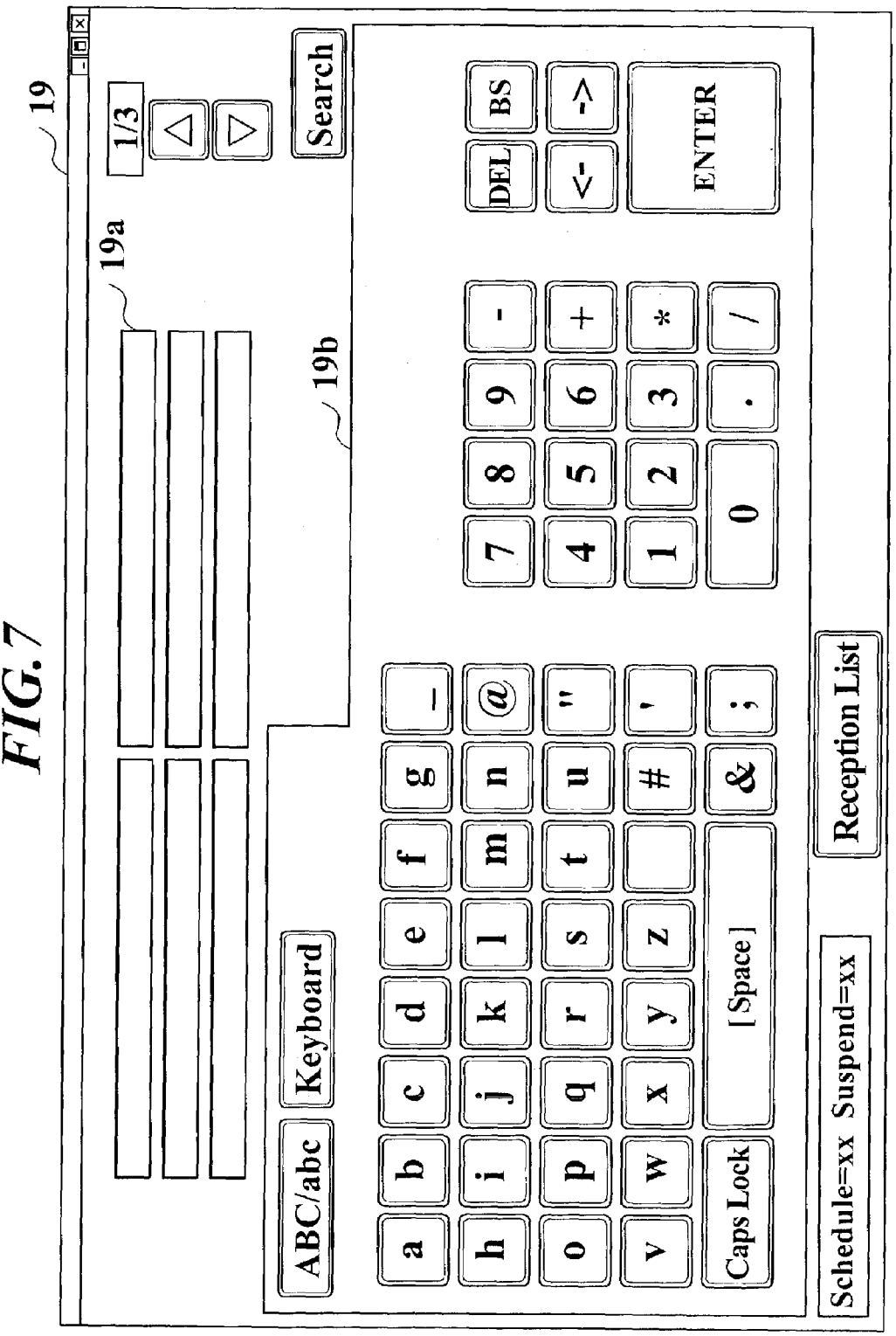
FIG. 7 is a view showing an example of a search screen displayed on the console according to the first embodiment of the present invention.
Figure 8:
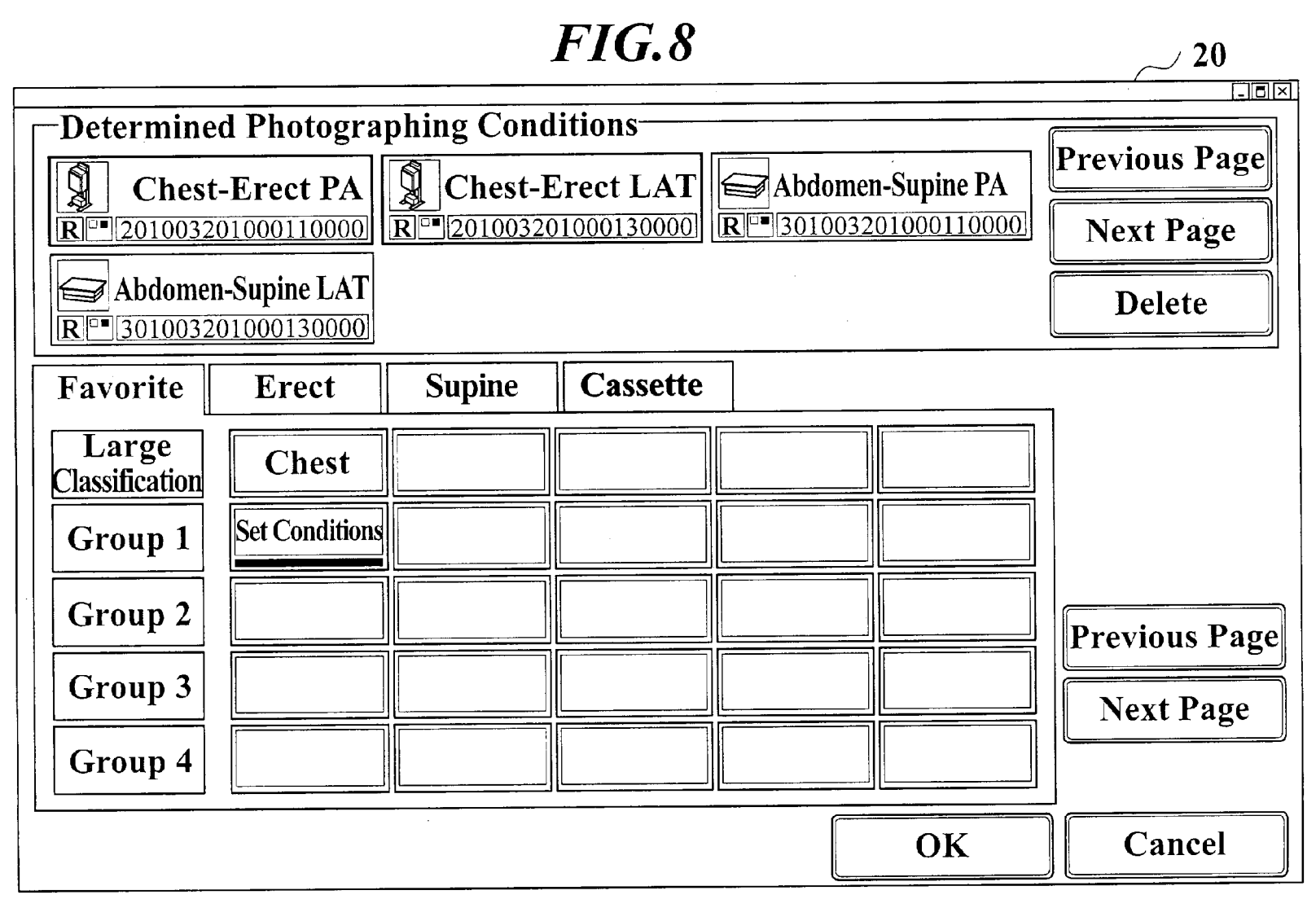

In the step S101, the photographing condition and the reading operation are inputted by using the display and operation section 12 of the console 3. These conditions are correlated with the cassette 17. Concretely, as an initial screen, for example, a reception list screen 18 for indicating photographing schedule information for patients is displayed on the display and operation section 12 as shown in FIG. 6. on the reception list screen 18, various information, such as patient ID, patient name, sex, age, department (such as internal medicine, surgery and the like), location, photographing condition, the sheet number of the photograph to be obtained and the like, is displayed in a list. Then, a predetermined patient to be photographed is selected from the reception list screen 18. Alternatively, one or more search conditions are inputted into input areas 19a of a search screen 19 to extract the predetermined patient. Thereafter, as shown in FIG. 8, a predetermined photographing condition is selected by using a photographing condition selecting screen 20.

In the photographing condition selecting screen 20, the previously set photographing conditions, the photographing conditions set by an operator, such as a radiation engineer, or the photographing conditions classified in each photographing style, are displayed. The operator selects a suitable photographing condition for the predetermined patient from those photographing condition. Not only the input of the photographing condition, but also the input of the reading condition (sampling pitch, reading sensibility or the like) for the obtained image data is carried out by using the reception list screen 18 and the like. The identification label information (plate ID) read from the cassette 17 by using the identification label detector 14 of the console 3 is correlated with the photographing condition and the reading condition.

Next, in the step S102, by using a known method, a selected patient is photographed with a radiographic image photographing device, such as an X-ray photographic device, and an X-ray transmission image of the patient is stored in the radiographic image conversion plate of the cassette 17 as a latent image.

When the operator, such as a radiation engineer, extracts the cassette 17 from the radiographic image photographing device and inserts the extracted cassette 17 into an optional slot of the reader 2, in case of the pre-registration, the plate ID is read by the identification label detector 9c of the reader 2 to search the reading condition in a database by using the plate ID as a search key, and to extract the reading condition corresponding to the plate ID. In case of the post-registration, after a cassette inserting order cue is correlated with a schedule selecting cue, the reading condition corresponding to the cassette 17 is extracted. Thereafter, in the step S103, the latent image of the radiographic image conversion plate is read by the reader 2 in accordance with the set reading condition.

In the process for reading the image data, the sensibility of the image reading section 9 is set in accordance with the value of the reading sensibility. The carrier speed of the plate carrier mechanism actuating part 7a and the sampling pitch of an A/D converter provided in the image reading section 9 are set. Then, the radiographic image conversion plate is withdrawn from the cassette 17. While the radiographic image conversion plate is carried in an X-direction by the sub-scanning mechanism actuating part 9a to execute the sub-scanning of the image, the image data stored and kept in the radiographic image conversion plate is read.

When the excitation light acts on the radiographic image conversion plate, the energy stored in the phosphor is generated as a stimulating light. The stimulating light is concentrated to convert the light into an electric signal by the image reading section 9. The electric signal is transformed logarithmically by a logarithmic transformer. Thereby, a linear electric signal which is linear to the light intensity of the stimulating light, is transformed to an electric signal which is logarithmically linear to the light intensity of the stimulating light, that is, an electric signal which is linear to the thickness. Further, the electric signal is converted into a digital one by the A/D converter.

A correction processing peculiar to the image reading section 9 and the radiographic image conversion plate (such as the shading correction for the image reading section 9, the unevenness correction for the unevenness caused by the excitation light generating section and the sensibility unevenness correction for the radiographic image conversion plate), a contrast transformation processing and the like are carried out for the image data outputted from the image reading section 9 by a processing section 11.

In the step S104, the operator selects the display format for the read image data. For example, a space for selecting the display format is provided in a photographing condition selecting screen 20. Alternatively, a screen for selecting the display format before the photographing condition selecting screen 20 is changed to one of the image data display screen 21 to 23, is provided. When the operator selects the display format, the selected format is extracted from the formats which are previously stored in the storage section 13. In the step S105, the display screen is prepared by fitting the image data into the extracted format.

Figure 9:
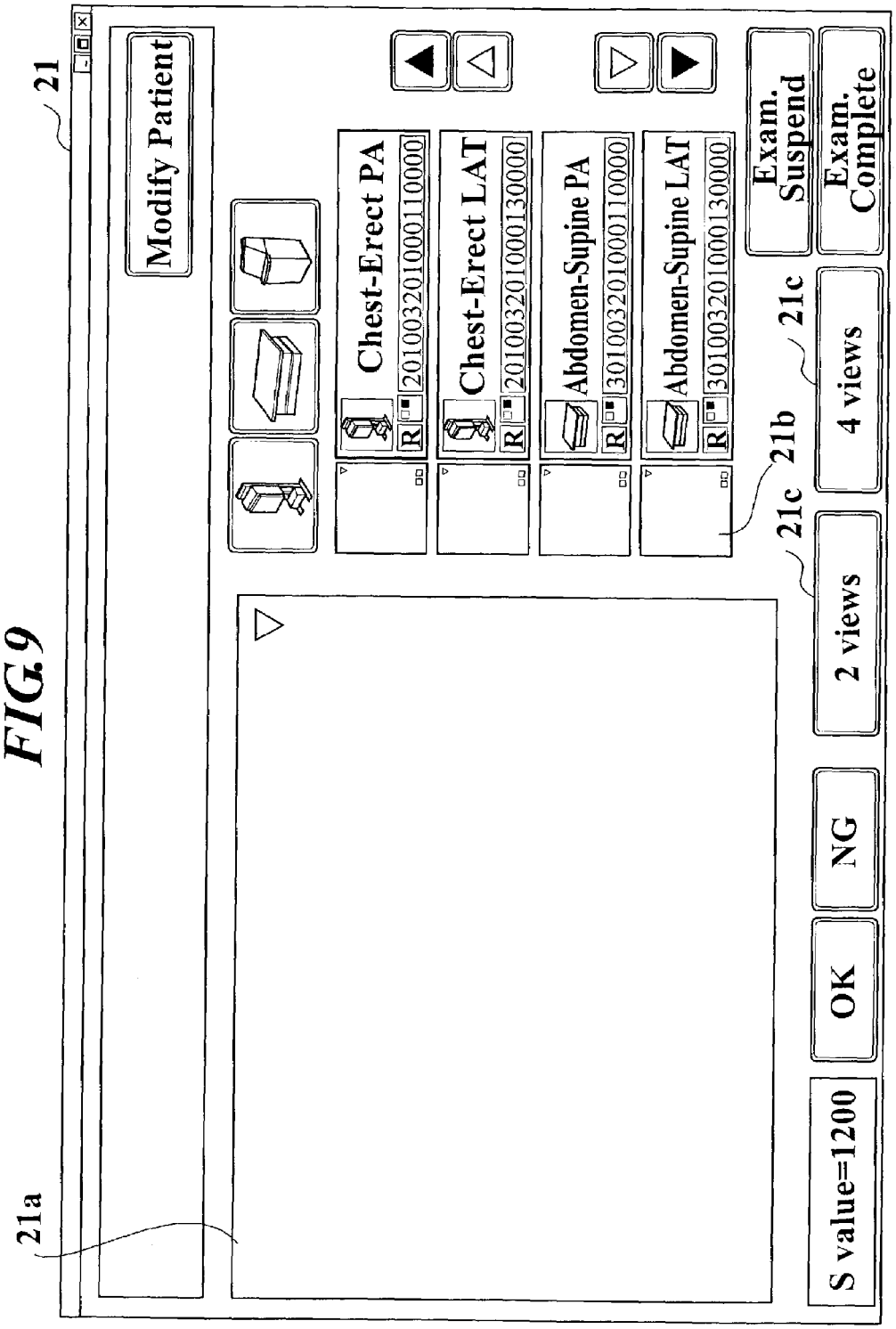
FIG. 9 is a view showing an example of an image data display screen (1 view display format) displayed on the console according to the first embodiment of the present invention.

As a display format, for example, as shown in FIG. 9, there is a display format having a main display section 21a for displaying a main image data and a sub display section 21b for displaying the related obtained image data in a reduced size in a thumbnail style. As shown in FIG. 10, there is a display format (4 views display) for largely displaying four image data in the same size. As shown in FIG. 11, there is a display format (2 views display) for largely displaying two image data in the same size. In addition, a display format (8 views display) for largely displaying eight image data in the same size, and the like are provided. The selected image data is displayed on the screen. The image data except the selected image data are displayed by changing the position and/or the size on the screen.

For example, in case of abdomen, head or other general photographing, the region is photographed independently. It is desirable that each image data is largely displayed. On the other hand, in case of the anteroposterior surface of the chest and the lateral surface of the chest, two image data are usually obtained and compared in the same size. Further, in case that the lumbar spine is photographed in four directions (anteroposterior surface, lateral surface, right oblique position and left oblique position), it is necessary to adjust each thickness of the image data obtained in four directions so as to be the same. It is desirable that the four image data can be compared in the same size. In case of the eight views display, because the image data are displayed in the same size and arrangement as ones obtained by photographing the patient with a film in a mass survey according to an earlier development, it is possible to use the image data without uncomfortableness. An operator can select a display format and display the image data in accordance with the condition of the patient and the region to be photographed so as to easily carry out the diagnosis.

As shown in FIG. 9, in the display format in which one image data is largely imaged, the display format can comprise one function selected between:

(a) a first function in which when an image data is obtained, the obtained image data is displayed in a large size (first size) and when another image data displayed in the second size which is smaller than the first size, is selected by an operator, the selected image data is displayed in the large size; and (b) a second function in which when the first image data is obtained, the obtained first image data is displayed in the second size and when the second image data displayed in the second size is selected by an operator, the selected image data is displayed in the large size.

In case of the function (a), it is possible to confirm the obtained image data in the large size without selecting the obtained image data one by one. In case of the function (b), it is possible to obtain one image data while the operator confirms another image data in the large size.

The display format is not limited to ones shown in the figures. The display format may have various configurations, such as a configuration that the optional number of image data are largely displayed in parallel or a configuration that one large image data, a plurality of middle image data and a plurality of small image data displayed in a thumbnail style are combined. In particular, the even number of image data are generally obtained in each direction, such as anteroposterior surface+lateral surface, right lateral surface+left lateral surface, right oblique position and left oblique position, to compare one with the others. By displaying the even number of image data, the field of the screen can be effectively used. Further, it is possible to optionally set the display size of each image data and the display position of each image data. In an initial display, the operator does not select the display format, and any one of the display formats may be automatically selected.

After the image data are displayed once, in the step S106, the operator judges whether the selected display format is suitable or not. When the selected display format is changed, in the step S107, a suitable display format is selected again to display the image data. The above step is repeatedly carried out until a display format which is suitable for the diagnosis is displayed. Thereafter, in the step S108, the patient is diagnosed by using the image data display screen 21 to 23.

When the display format is changed, in addition to each image data display screen, a switch (for example, a changing switch 21c shown in FIG. 9, a changing switch 22a shown in FIG. 10 and a changing switch 23a shown in FIG. 11) for changing one display form to another is provided so as to be able to directly change the display format.

By providing such a changing function for changing one display format to another, when the image data is largely displayed one by one, for example, in the case of pneumonia or the like, it is possible to freely change the display format in accordance with the object and to diagnose the patient accurately. Further, when the images are not used separately and a plurality of images are compared with each other, and it is judged whether the images are obtained in a correct position and in a suitable contrast, such as a case that the lumbar spine is photograhed in four directions (anteroposterior surface, lateral surface, right oblique position and left oblique position), it is possible to compare the image data during the photographing by applying the display format selecting unit according to the present invention to the radiographic image photographing device. Therefore, it is possible to carry out the feedback, such as to adjust the contrast during the photographing and to adjust the position in the next photographing.

As described above, in the image reading device according to the present embodiment and the method for displaying the image data in the device, a plurality of display formats, such as a display format comprising a main screen and a thumbnail screen, a display format for displaying the optional number (such as two, four or the like) of screens in parallel and the like, are previously stored as the display formats for the image data. It is possible to display the image data read in accordance with the operator's select. The display format can be freely changed. Because a patient is diagnosed by using the image data displayed in a format which is suitable for the patient and the region to be photographed, the accuracy of the diagnosis is improved. The diagnosis time can be shortened. It is possible to support the diagnosis of a radiation engineer and that of a doctor.

Figure 13:
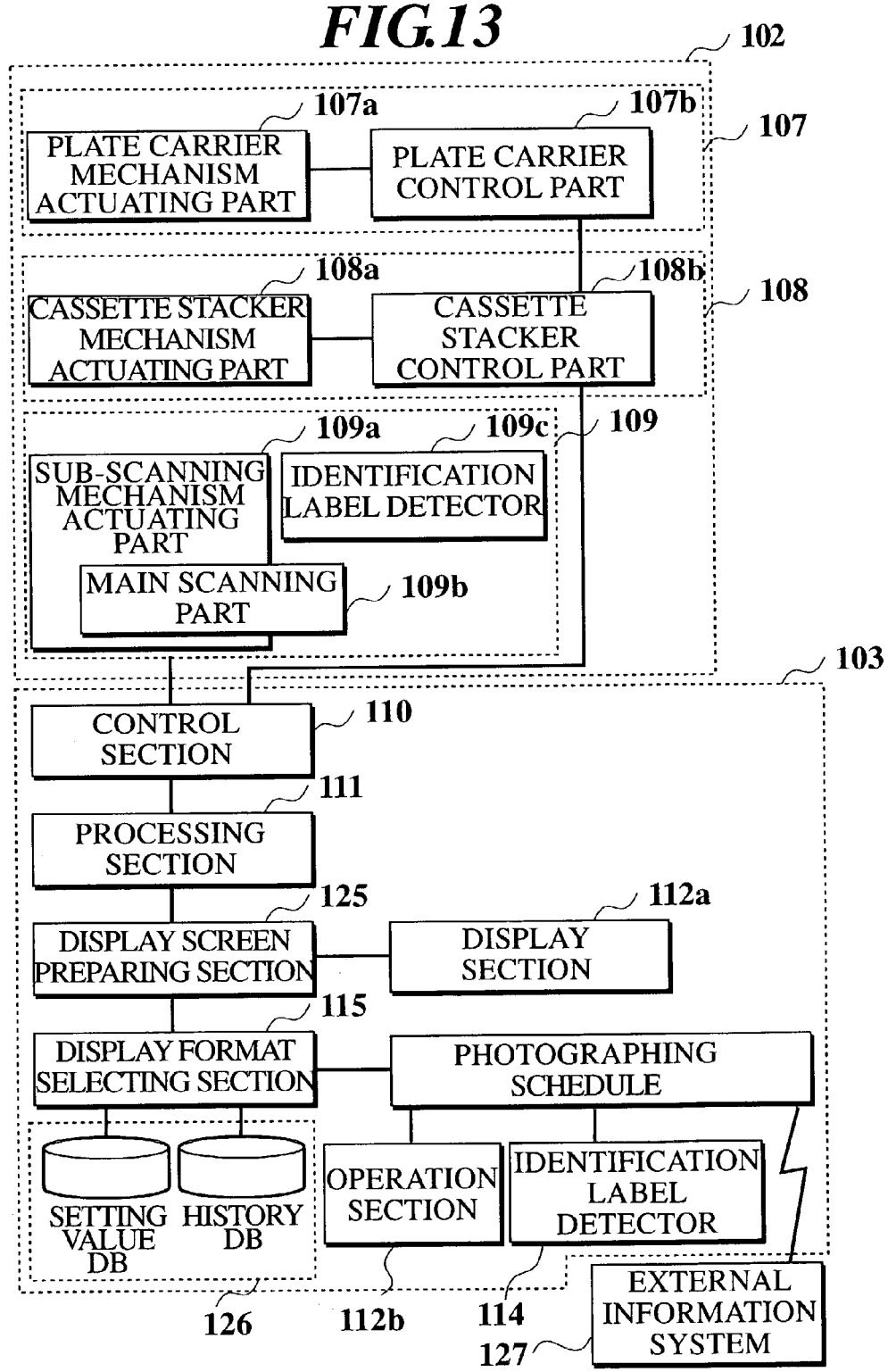
FIG. 13 is a block diagram showing an arrangement of the reader and that of the console according to the second embodiment of the present invention.
Figure 14:
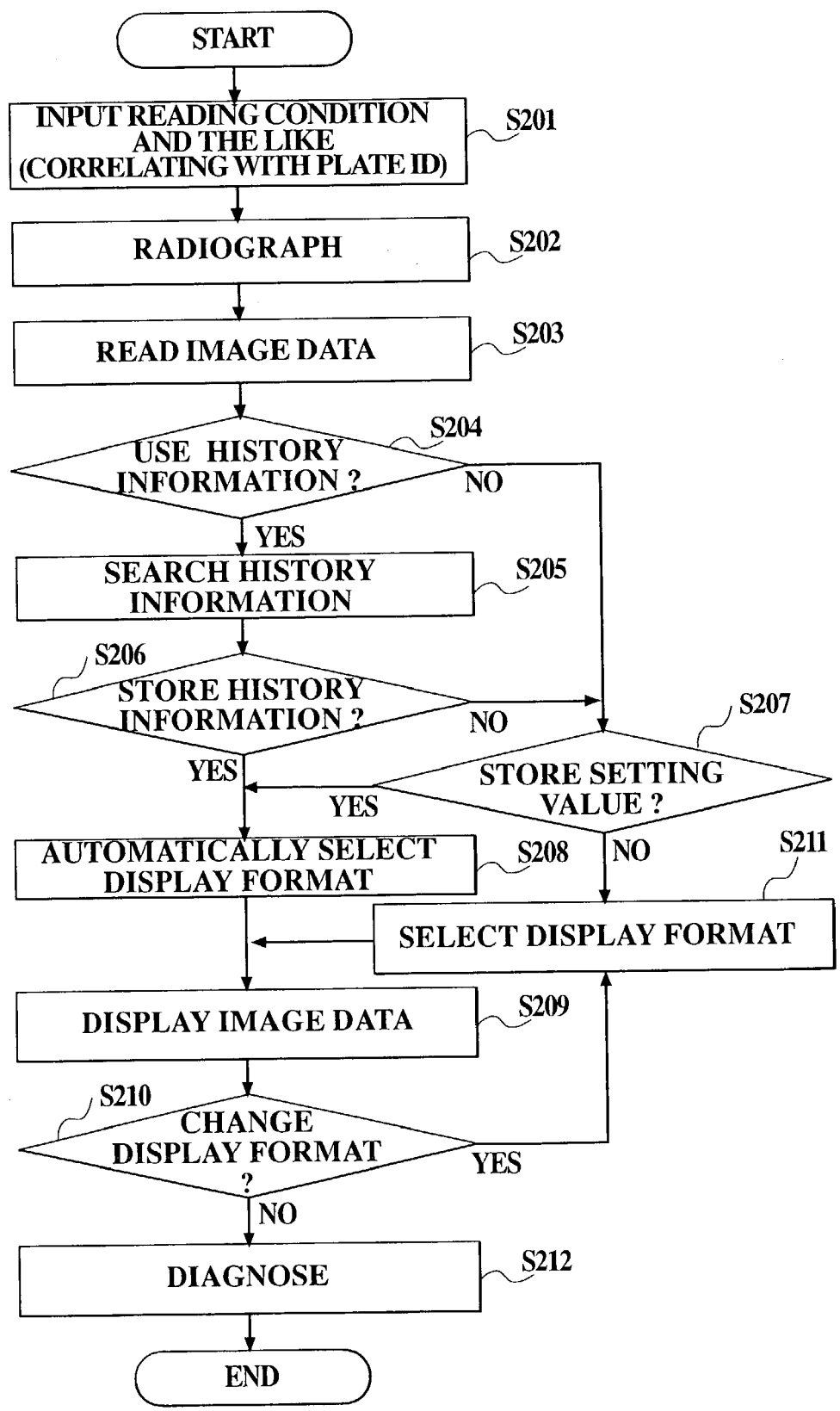
FIG. 14 is a flowchart showing a process for the image displaying method according to the second embodiment.
Figure 15:
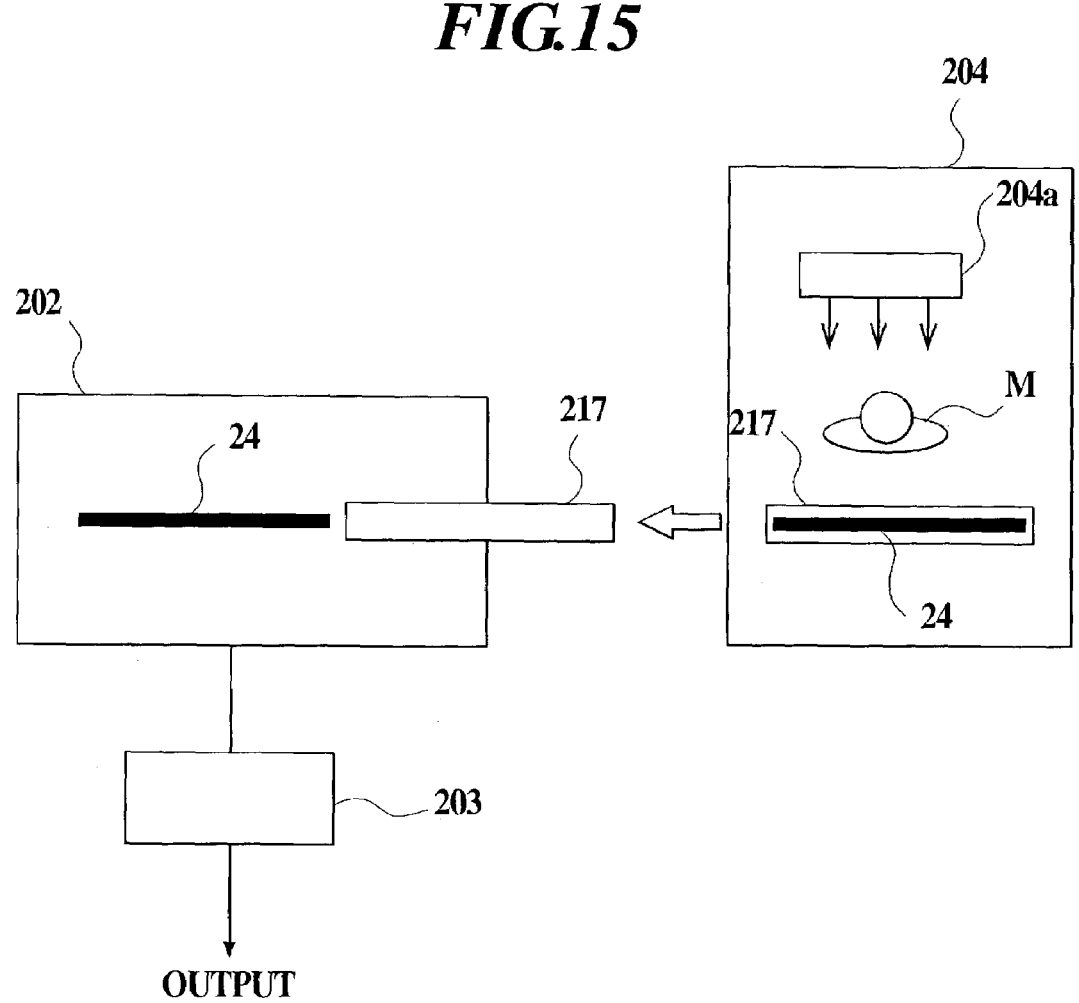
FIG. 15 is a schematic view showing an arrangement of an radiographic image diagnostic system according to an earlier development.

Second Embodiment:

An image obtaining and displaying device (image reading device) according to the second embodiment of the present invention, a method for displaying a plurality of image data in the device and a display format selecting program will be explained with reference to FIGS. 13 and 14. FIG. 13 is a block diagram showing an arrangement of the image reading device (the reader and the console) according to the second embodiment. FIG. 14 is a flowchart showing a process for the image displaying method according to the present embodiment. In the present embodiment, it is described that the display format for the image data is automatically selected by using a display format selecting program.

That is, in the first embodiment, an operator, such as a radiation engineer, considers the condition of a patient, a region to be photographed and the like and selects a display format for the image data. However, in general, when the patient and the region to be photographed are the same, the display format is usually the same. For example, in case that the same patient is photographed again, when the image data obtained last time were displayed such as in 4 views display, it is appropriate that the image data obtained this time are displayed in 4 views display. Even though a different patient is photographed, it is appropriate that the display format is the same when the region to be photographed is the same. Further, when a plurality of radiographic image photographing device are disposed, it is appropriate that the image data obtained by the same device are displayed in the same display format.

In the present embodiment, as shown in FIG. 13, the console 103 comprises a processing section 111 for carrying out various image processing for the image read by the reader 2; a display section 112a and an operation section 112b for displaying a reception list, image data and the like, for setting patient information, region-to-be-photographed information, a reading condition or the like and for selecting a display format; and an identification label detector 114 for reading a plate ID of a cassette 117. Further, the console 103 comprises a storage section 126 for storing the display formats, photographing history information, setting information and the like, a display screen preparing section 125 for preparing a display screen and a display format selecting section 115 for searching a display format which is adopted in a previous photographing, from the photographing history information and the setting information. The display format selecting section 115 comprises a program for automatically selecting a suitable display format in accordance with the result of the above search. By executing the display format selecting program, a suitable display format is automatically selected. With respect to the reader 102 and the console 103, the control section for the reader 102 is provided in the console 103 (FIG. 13). However, the control section 110 may be incorporated into the reader 102. The processing section 111 may be also provided in the reader 102. Further, the reader 102 and the console 103 may be combined.

Hereinafter, with reference to the flowchart shown in FIG. 14, the process from the X-ray photographing for a patient to the displaying of the X-ray image on the console 103, will be explained.

Firstly, like the above-described first embodiment, in the step S201, the photographing condition and the reading operation are inputted by using the display and operation section 112 of the console 103. These conditions are correlated with the cassette 117. In the step S202, by using a known method, a patient is photographed with a radiographic image photographing device, such as an X-ray photographic device, and an X-ray transmission image of the patient is stored in the radiographic image conversion plate of the cassette 117 as a latent image.

Thereafter, in the step S203, the latent image of the radiographic image conversion plate is read by the reader 102 in accordance with the set reading condition. A correction processing peculiar to the image reading section 109 and the radiographic image conversion plate (such as the shading correction for the image reading section 109, the unevenness correction for the unevenness caused by the excitation light generating section and the sensibility unevenness correction for the radiographic image conversion plate), a contrast transformation processing and the like are carried out for the image data outputted from the image reading section 109 by a processing section 111.

In the above-described first embodiment, the operator selects a display format. However, in the present embodiment, by the display format selecting program, the history information and the setting information corresponding to the photographing to be carried out is searched from the history information and the setting information stored in the storage section 113. For example, as the history information or the setting information, there is a reading unit, a image display terminal, a type of the diagnostic image conversion medium, a type of a cassette, date and time of the photographing, an operator, supplementary information of a schedule for the photographing or the like (the reading unit and the image display unit can be specified by using an IP address of the network, MAC address, a serial number registered to the unit, a name registered to the unit or the like, and the cassette and the diagnostic image conversion medium can be specified by using a bar cord, an IC chip or the like.). As the supplementary information of a schedule for the photographing, there is the number of image data to be obtained, a region to be photographed, a name of a doctor, a department or the like. The corresponding history information and the corresponding setting information are extracted by using the above information as a search key. The display format selected in the previous photographing is specified from the extracted information.

The reasons why the above information is used are as follows.

(1) Reading unit, image display terminal: In each hospital, there is away to suitably display the image data. In a large hospital, a different radiographing room is used at each department, such as orthopedics department, internal medicine department or the like. Because there are various ways to suitably display the image data, a specific reading unit, a suitable display format to be displayed in the display unit are different.

(2) Type of cassette: A type of the cassette to be used differs in a specified region to be photographed, such as radiation therapy, mammography or the like. Because the types of the cassette are different, the ways to display the image data are different.

(3) Operator: Each engineer has a favorite way to use the system.

(4) Date and time: There is some possibility that the ways to use the system differ in specified days of the week, such as weekend or the like.

(5) Number of the sheets of the image data to be obtained:

There are some cases that it is preferable that the number of the sheets to be displayed is automatically changed in accordance with the number of the sheet of the image data to be obtained. For example, in case of a hospital in which it is preferable that the image is displayed as largely as possible and that the minimum required number of the sheets of the image data to be displayed more largely than a certain size at the same time is large, when one image data is obtained, the system is controlled so as to select the display format that one image data is largely displayed and the other image data are displayed in a reduced size. When two image data are obtained, the display format that the two image data are displayed at the same time, is selected. When three or four image data are obtained, the display format that four image data are displayed at the same time, is selected. When five or more image data are obtained, the display format that four image data are displayed at the same time, is selected.

(6) Doctor: Because there are a requested doctor, a radiographic image interpreting doctor and the like in a hospital and each doctor belongs to each department, the region to be photographed is roughly determined.

(7) Department: From the department in which the photographing is carried out, the region to be photographed is roughly determined.

Concretely, in the step S204, a user selects whether the history information is used or not. When the history information is used, in the step S205, the corresponding history information is searched. In the step S206, it is judged whether the history information exists. When the history information is not used, in the step S207, it is judged whether the setting value exists. When the history information is not used and the setting value does not exist, in the step S211, the operator selects a display format. When the history information or the setting value exists, in the step S208, the display format is automatically selected. For example, the data relating to the same region to be photographed as the present photographing is extracted from the history information. When the display format is the same as that of the previous photographing, the same display format is selected. When a plurality of display formats are adopted, the display format which is adopted most frequently, is selected- The corresponding display format selected from a plurality of formats which are previously stored in the storage section 126, is extracted. In the step S207, the display screen is prepared by fitting the image data into the extracted format.

As a display format, like the first embodiment, as shown in FIG. 9, as shown in FIG. 9, there is a display format having a main display section 21a for displaying a main image data and a sub display section 21b for displaying the related obtained image data in a reduced size in a thumbnail style. As shown in FIG. 10, there is a display format (4 views display) for largely displaying four image data in the same size. As shown in FIG. 11, there is a display format (2 views display) for largely displaying two image data in the same size. In addition, a display format (8 views display) for largely displaying eight image data in the same size, and the like are provided. By selecting the same display format as the previous photographing in accordance with the history information, the display format which is suitable for the condition of the patient and the region to be photographed is automatically selected.

After the image data are displayed once in the step S209, in the step s210, the operator judges whether the display format which is automatically selected is suitable or not. When the selected display format is changed, in the step S211, a suitable display format is selected again to display the image data. Thereafter, in the step S212, the patient is diagnosed by using the image data display screen 21 to 23.

As described above, in the image obtaining and displaying device according to the present embodiment and the method for displaying the image data in the device, because the display format which is suitable for the condition of the patient and the region to be photographed, is automatically selected from a plurality of display formats in accordance with the history information and the setting information, the operator is not required to select the display format in each image reading operation. After the display format is automatically selected, the display format can be freely changed. Therefore, the accuracy of the diagnosis is improved.

The diagnostic image pickup device for obtaining a diagnostic image is not limited to a radiographic image photographing device, such as an X-ray radiographing device or the like, and includes an optional diagnostic image pickup device which is used in a medical field, such as a device for photographing a patient by using magnetism, supersonic waves, or the like. In the above embodiments, it is described that the radiographic image data is read from the radiographic image conversion plate. However, in the method for reading the image data from the other diagnostic image conversion medium storing the diagnostic image, a suitable method which is known to a skilled person in the art is adapted.

As explained above, according to the medical image displaying device, the image obtaining and displaying device according to the present invention, the method for displaying the image in the displaying device and the display format selecting program, the following effect can be obtained.

The first effect of the present invention is that the display format of the image data, which is suitable for the diagnosis can be selected in accordance with the condition of the patient and the region to be photographed.

The reason thereof is as follows. A plurality of display formats, such as a display format comprising one large screen and a plurality of reduced screens, a display format for largely displaying a plurality of image data in parallel and the like, are stored in the storage section of the image obtaining and displaying device. It is possible to select the display format which is suitable for the diagnosis, in accordance with the operator's select.

The second effect of the present invention is that the display format of the image data, which is suitable for the diagnosis can be automatically set.

The reason thereof is as follows. By executing the display format selecting program, the display format which is suitable for the diagnosis is selected in accordance with the reading unit, the image display unit, a type of the diagnostic image conversion medium, a type of a cassette, date and time of the photographing, an operator, supplementary information of a schedule for the photographing or the like, and the photographing history information or the setting information which is correlated with the selected display format.

After the display format is automatically or manually set, one display format can be freely changed to another. Therefore, it is possible to improve the accuracy of the diagnosis regardless of the condition of the patient and the region to be photographed. It is possible to support a radiation engineer, a doctor or the like.

The entire disclosure of Japanese Patent Application No. Tokugan 2002-19406 filed on Jan. 29, 2002 including specification, claims drawings and summary are incorporated herein by reference in its entirety.

What is claimed is:

1. A medical image displaying device for displaying a plurality of images of a patient, said medical image displaying device comprising:
a plurality of selectable display formats for displaying each of the plurality of images in a predetermined display size and at a predetermined display position on a screen;
wherein one of the plurality of display formats is automatically selected in accordance with a number of the images to be obtained and in accordance with a region to be photographed of the patient corresponding to the images to be obtained, and
the plurality of imaqes are displayed on the screen in accordance with the selected displayed format.

2. The medical image displaying device according to claim 1, wherein each of the plurality of display formats comprises a screen changing section for instructing the device to change one display format to another display format on the screen.

3. The medical image displaying device according to claim 1, wherein the plurality of display formats comprise:
a first display format in which one image is displayed in a first size and at least one other image is displayed in a second size which is smaller than the first size; and
a second display format in which the plurality of images are displayed in a same size.

4. The medical image displaying device according to claim 3, wherein a first obtained image is displayed in the first size and a second obtained image is displayed in the second size, and when the second obtained image is selected, the selected second obtained image is displayed in the first size.

5. The medical image displaying device according to claim 3, wherein a first obtained image and a second obtained image are displayed in the second size; and
wherein when one of the first obtained image and the second obtained image is selected, the selected one of the first obtained image and the second obtained image is displayed in the first size.

6. The medical image displaying device according to claim 3, wherein the second display format comprises at least one parallel display format for displaying in parallel an even number of images selected from the plurality of images.

7. The medical image displaying device according to claim 6, wherein the at least one parallel display format comprises:
a first parallel display format for displaying in parallel two images selected from the plurality of images;

a second parallel display format for displaying in parallel four images selected from the plurality of images; and a third parallel display format for displaying in parallel eight images selected from the plurality of images.

8. The medical image displaying device according to claim 6, wherein in the at least one parallel display format, images other than the selected even number of images are displayed by changing at least one of the predetermined image display size and the predetermined image display position on the screen.

9. The medical image displaying device according to claim 1, wherein the plurality of display formats comprise a display format in which the plurality of images are displayed in a same size.

10. An image obtaining and displaying device comprising:
  a reading unit for reading a plurality of image data of a patient from a diagnostic image conversion medium for storing diagnostic images; and
  a display unit for displaying a plurality of images corresponding to the plurality of image data, said display unit comprising:
    a storing section for storing a plurality of selectable display formats for displaying each of the plurality of images in a predetermined display size and at a predetermined display position on a screen;
    a selecting section for automatically selecting one of the display formats in accordance with a number of the images to be obtained and in accordance with a region to be photographed of the patient corresponding to the images to be obtained; and
    a display section for displaying the images on a display screen in accordance with the selected display format.

11. The image obtaining and displaying device according to claim 10, wherein each of the plurality of display formats comprises a screen changing section for instructing the device to change one display format to another display format on the screen.

12. The image obtaining and displaying device according to claim 10, wherein history information is stored in the storing section, and the history information correlates at least one of the display formats with at least one of: the reading unit, the display unit, a type of the diagnostic image conversion medium, a type of a cassette, a date and time of imaging, an operator, and supplementary information of a schedule for the imaging; and
  wherein the selecting section comprises a corresponding display format selecting section for selecting a display format which corresponds to the history information.

13. The image obtaining and displaying device according to claim 10, wherein setting information is previously registered in the storing section, and the setting information correlates at least one of the display formats with at least one of: the reading unit, the display unit, a type of the diagnostic image conversion medium, a type of a cassette, a date and time of imaging, an operator, and supplementary information of a schedule for the imaging; and
  wherein the selecting section comprises a corresponding display format selecting section for selecting a display format which corresponds to the setting information.

14. The image obtaining and display device according to claim 12, wherein the supplementary information comprises at least one of a name of a doctor, and a department.

15. The image obtaining and display device according to claim 10, wherein the plurality of display formats comprise:
  a first display format in which one image is displayed in a first size and at least one other image is displayed in a second size which is smaller than the first size; and
  a second display format in which the plurality of images are displayed in a same size.

16. The image obtaining and display device according to claim 15, wherein a first obtained image is displayed in the first size and a second obtained image is displayed in the second size, and when the second obtained image is selected, the selected second obtained image is displayed in the first size.

17. The image obtaining and display device according to claim 15, wherein a first obtained image and a second obtained image are displayed in the second size; and
  wherein when one of the first obtained image and the second obtained image is selected, the selected one of the first obtained image and the second obtained image is displayed in the first size.

18. The image obtaining and display device according to claim 15, wherein the second display format comprises at least one parallel display format for displaying in parallel an even number of images selected from the plurality of images.

19. The image obtaining and display device according to claim 18, wherein the at least one parallel display format comprises:
  a first parallel display format for displaying in parallel two images selected from the plurality of images;
  a second parallel display format for displaying in parallel four images selected from the plurality of images; and
  a third parallel display format for displaying in parallel eight images selected from the plurality of images.

20. The image obtaining and display device according to claim 18, wherein in the at least one parallel display format, images other than the selected even number of images are displayed by changing at least one of the predetermined image display size and the predetermined image display position on the screen.

21. The image obtaining and display device according to claim 10, wherein the plurality of display formats comprise a display format in which the plurality of images are displayed in a same size.

22. A method for displaying a plurality of images of a patient with a medical image displaying device, said method comprising:
  providing a plurality of selectable display formats for displaying each of the plurality of images in a predetermined display size and at a predetermined display position on a screen;
  automatically selecting one of the plurality of display formats in accordance with a number of the images to be obtained and in accordance with a region to be photographed of the patient corresponding to the images to be obtained; and
  displaying the plurality of images on the screen in accordance with the selected display format.

23. The method for displaying the plurality of images according to claim 22, wherein each of the plurality of display formats comprises a screen changing section for instructing the device to change one display format to another display format on the screen.

24. The method for displaying the plurality of images according to claim 22, wherein the plurality of display formats comprise:
  a first display format in which one image is displayed in a first size and at least one other image is displayed in a second size which is smaller than the first size; and a second display format in which the plurality of images are displayed in a same size.

25. The method for displaying the plurality of images according to claim 24, wherein a first obtained image is displayed in the first size and a second obtained image is displayed in the second size, and when the second obtained image is selected, the selected second obtained image is displayed in the first size.

26. The method for displaying the plurality of images according to claim 24, wherein a first obtained image and a second obtained image are displayed in the second size; and
wherein when one of the first obtained image and the second obtained image is selected, the selected one of the first obtained image and the second obtained image is displayed in the first size.

27. The method for displaying the plurality of images according to claim 24, wherein the second display format comprises at least one parallel display format for displaying in parallel an even number of images selected from the plurality of images.

28. The method for displaying the plurality of images according to claim 27, wherein the at least one parallel display format comprises:
a first parallel display format for displaying in parallel two images selected from the plurality of images;
a second parallel display format for displaying in parallel four images selected from the plurality of images; and
a third parallel display format for displaying in parallel eight images selected from the plurality of images.

29. The method for displaying the plurality of images according to claim 27, wherein in the at least one parallel display format, images other than the selected even number of images are displayed by changing at least one of the predetermined image display size and the predetermined image display position on the screen.

30. The method for displaying the plurality of images according to claim 22, wherein the plurality of display formats comprise a display format in which the plurality of images are displayed in a same size.

31. A method for displaying a plurality of images of a patient corresponding to image data read by an image data reading device from a diagnostic image conversion medium for storing the plurality of images, said method comprising:
storing a plurality of selectable display formats for displaying each of the plurality of images in a predetermined display size and at a predetermined display position on a screen;
selecting one of the plurality of display formats; and
displaying the images on a display screen in accordance with the selected display format;
wherein the one of the plurality of display formats is automatically selected in accordance with a number of the images to be obtained and in accordance with a region to be photographed of the patient corresponding to the images to be obtained.

32. The method for displaying the plurality of images according to claim 31, wherein the one of the display formats is selected based on history information which correlates at least one of the plurality of display formats with at least one of: the image reading device, an image display terminal, a type of the diagnostic image conversion medium, a type of a cassette, a date and time of imaging, an operator, and supplementary information of a schedule for the imaging.

33. The method for displaying the plurality of images according to claim 31, wherein the one of the display formats is selected based on previously registered setting information which correlates at least one of the plurality of display formats with at least one of: the image reading device, an image display terminal, a type of the diagnostic image conversion medium, a type of a cassette, a date and time of imaging, an operator, and supplementary information of a schedule for the imaging.

34. The method for displaying the plurality of images according to claim 32, wherein the supplementary information comprises at least one of a name of a doctor, and a department.

* * * * *